US010665002B2

(12) United States Patent
Lou et al.

(10) Patent No.: US 10,665,002 B2
(45) Date of Patent: May 26, 2020

(54) RECONSTRUCTING IMAGE

(71) Applicant: Shanghai Neusoft Medical Technology Co., Ltd., Shanghai (CN)

(72) Inventors: Shanshan Lou, Shenyang (CN); Lixia Tong, Shenyang (CN)

(73) Assignee: Shanghai Neusoft Medical Technology Co., Ltd., Shanghai (CN)

(*) Notice: Subject to any disclaimer, the term of this patent is extended or adjusted under 35 U.S.C. 154(b) by 148 days.

(21) Appl. No.: 15/964,627

(22) Filed: Apr. 27, 2018

(65) Prior Publication Data
US 2018/0315224 A1 Nov. 1, 2018

(30) Foreign Application Priority Data

Apr. 27, 2017 (CN) .......................... 2017 1 0288356

(51) Int. Cl.
*A61B 6/00* (2006.01)
*G06T 11/00* (2006.01)
*A61B 6/03* (2006.01)

(52) U.S. Cl.
CPC .......... *G06T 11/006* (2013.01); *G06T 11/005* (2013.01); *A61B 6/032* (2013.01);
(Continued)

(58) Field of Classification Search
CPC ...... G06T 11/00; G06T 11/003; G06T 11/005; G06T 11/006; G06T 2207/10081;
(Continued)

(56) References Cited

U.S. PATENT DOCUMENTS

| 5,270,923 A | * | 12/1993 | King | A61B 6/032 382/131 |
| 6,490,335 B1 | * | 12/2002 | Wang | A61B 6/032 378/15 |
| 2007/0140535 A1 | | 6/2007 | Li et al. | |

FOREIGN PATENT DOCUMENTS

| CN | 1895174 A | 1/2007 |
| CN | 102440799 A | 5/2012 |

(Continued)

OTHER PUBLICATIONS

State Intellectual Property Office of the People's Republic of China, Office Action and Search Report Issued in Application No. 201710288356.3, dated Oct. 23, 2019, 19 pages, (Submitted with English-language Machine Translation).

*Primary Examiner* — Jurie Yun
(74) *Attorney, Agent, or Firm* — Fish & Richardson P.C.

(57) ABSTRACT

Methods, devices and apparatus for reconstructing an image are provided. In one aspect, a method includes: determining an initial angle and a final angle of an X-ray tube and a pitch value when a helical-half-scan is to be performed, obtaining scanning data of each of reconstructing points in a reconstructing position by performing the helical-half-scan on a detected region of a subject based on the determined initial angle, the final angle and the pitch value, determining a respective half-scan-weight and a respective helical weight of each of the reconstructing points in the reconstructing position, obtaining weighted data by performing weighting on the scanning data of each of the reconstructing points with respective the half-scan-weight and the respective helical weight of the reconstructing point, and reconstructing a Computed Tomography (CT) image of the reconstructing position by performing back-projection on the weighted data.

20 Claims, 7 Drawing Sheets

(52) U.S. Cl.
CPC ....... *A61B 6/54* (2013.01); *G06T 2207/10081* (2013.01); *G06T 2211/421* (2013.01)

(58) Field of Classification Search
CPC ....... G06T 2211/40; A61B 6/00; A61B 6/032; A61B 6/542; A61B 6/027; A61B 6/5205; A61B 6/5211; A61B 6/5294
USPC ............... 378/4, 8, 15, 16, 19, 901; 382/131
See application file for complete search history.

(56) References Cited

FOREIGN PATENT DOCUMENTS

| | | |
|---|---|---|
| CN | 102596040 A | 7/2012 |
| CN | 102711619 A | 10/2012 |
| CN | 104224220 A | 12/2014 |
| CN | 105615912 A | 6/2016 |
| JP | 2011136219 A | 7/2011 |

* cited by examiner

Moving direction of the scanning bed

RECONSTRUCTING IMAGE

CROSS REFERENCE TO RELATED APPLICATIONS

This application claims priority to Chinese Patent Application 201710288356.3 filed on Apr. 27, 2017, the entire content of which is incorporated herein by reference.

TECHNICAL FIELD

The present disclosure relates to methods and devices for reconstructing an image in the technical field of Computed Tomography (CT).

BACKGROUND

Scanning modes of a CT device may include an axial scan and a helical scan. The axial scan refers to a scan in which a scanning bed firstly moves to a first scanning position, and then an X-ray tube begins emitting X-rays to perform scanning (hereinafter referred to as ray-emitting scan); when the scanning for the first scanning position is finished, the scanning bed moves to a second scanning position, and then the X-ray tube begins to perform the ray-emitting scan again. Therefore, scanning speed of the axial scan is relatively slow, and resolution of a reconstructed image obtained by the axial scan is relatively low in a movement direction (hereinafter referred to as z-direction) of the scanning bed.

The helical scan refers to a scan in which a scanning bed moves forward at a particular speed when a gantry of a CT device rotates. Therefore, scanning speed of the helical scan is relatively fast, and resolution of a reconstructed image obtained by the helical scan is relatively high in the z-direction. In the helical scan, the X-ray tube mounted on the gantry keeps emitting X-rays when the gantry rotates.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, devices and apparatus for reconstructing images in the technical field of Computed Tomography (CT), particularly for helical-half-scans.

One aspect of the subject matter described in the present disclosure can be embodied in methods that include the actions of determining an initial angle and a final angle of an X-ray tube and a pitch value when a helical-half-scan is to be performed, the helical-half-scan referring to a helical scan in which the X-ray tube emits X-rays between the initial angle and the final angle during one circle of rotation of a gantry; obtaining scanning data of each of reconstructing points in a reconstructing position by performing the helical-half-scan on a detected region of a subject based on the determined initial angle, the final angle and the pitch value; determining a respective half-scan-weight and a respective helical weight of each of the reconstructing points in the reconstructing position; obtaining weighted data by performing weighting on the scanning data of each of the reconstructing points with respective the half-scan-weight and the respective helical weight of the reconstructing point; and reconstructing a Computed Tomography (CT) image of the reconstructing position by performing back-projection on the weighted data.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination.

In some implementations, the actions further include: determining that the helical-half-scan is to be performed by determining that the detected region of the subject contains a skip region without X-ray radiation. Determining the initial angle and the final angle of the X-ray tube can include: determining a position of the skip region; and determining the initial angle and the final angle of the X-ray tube based on the position of the skip region. An absolute value of a difference between the initial angle and the final angle of the X-ray tube is equal to or greater than a preset angle threshold, and the obtained scanning data during one circle of rotation of the gantry is sufficient for reconstructing the CT image of the reconstructing position.

In some implementations, the actions further include: determining that the helical-half-scan is to be performed by determining that a dual-energy scan is to be performed on the detected region of the subject. Determining the initial angle and the final angle of the X-ray tube can include: selecting a kilovolt switching time length of the dual-energy scan; determining a ray-emitting angle interval length of the X-ray tube based on the kilovolt switching time length; and determining two angles as the initial angle and the final angle of the X-ray tube, respectively. An absolute value of a difference of the two angles is smaller than the ray-emitting angle interval length and equal to or greater than a preset angle threshold, and the obtained scanning data during one circle of rotation of the gantry is sufficient for reconstructing the CT image of the reconstructing position.

Determining the pitch value can include: determining a maximum pitch value based on a reconstructing field of view of a CT device, a radius of rotation of the X-ray tube, a number of slices of a detector of the CT device and a single-slice thickness of the detector; and determining a value less than the maximum pitch value as the pitch value. When the helical-half-scan is performed according to the maximum pitch value, the obtained scanning data during one circle of rotation of the gantry can be sufficient for reconstructing the CT image of the reconstructing position.

In some implementations, determining the half-scan-weight and the helical weight of the reconstructing point includes: determining whether the scanning data of the reconstructing point satisfies a preset image reconstructing condition; and in response to determining that the scanning data of the reconstructing point satisfies the preset image reconstructing condition, determining the half-scan-weight and the helical weight of the reconstructing point.

In some cases, determining whether the scanning data of the reconstructing point satisfies the preset image reconstructing condition includes: determining the scanning data of the reconstructing point corresponding to a same energy level as second scanning data; determining a sampling angle of the second scanning data at each of sampling views; generating a slice position of the sampling angle relative to the reconstructing point based on a coordinate of the reconstructing point, a radius of rotation of the X-ray tube, a number of slices of a detector of a CT device and a single-slice thickness of the detector; and determining whether the second scanning data satisfies the preset image reconstructing condition based on the slice position of the sampling angle relative to the reconstructing point.

In some cases, determining whether the second scanning data satisfies the preset image reconstructing condition based on the slice position of the sampling angle relative to the reconstructing point includes: determining a number of valid sampling angles of the reconstructing point based on the slice position of each of the sampling angles relative to the reconstructing point; and determining whether the second scanning data satisfies the preset image reconstructing condition by determining whether the number of the valid sampling angles is greater than or equal to a preset number threshold. The actions can further include: determining a number of sampling angles each of which the slice position is no less than 0 and no greater than the number of slices of the detector minus 1, and in response, defining the number of the sampling angles as the number of valid sampling angles of the reconstructing point.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Figure 1A:
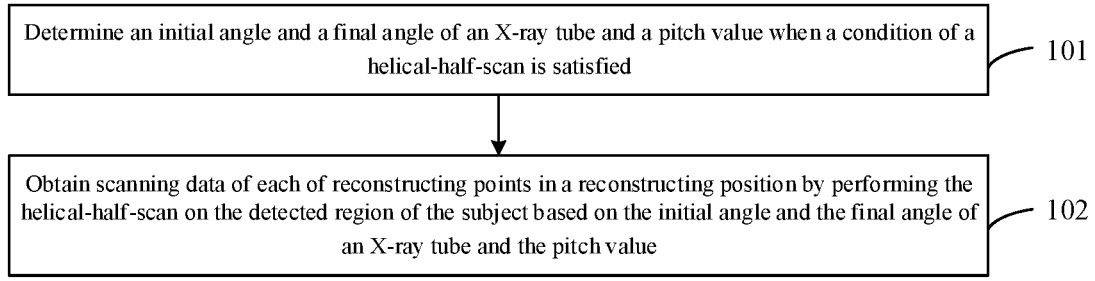
FIG. 1A is a flowchart illustrating a process of a helical-half-scan method of obtaining scanning data of a reconstructing point, according to an example of the present disclosure.

In the present disclosure, when performing a scan with a CT device, scanning data of each of reconstructing points in a reconstructing position within a detected region of a subject may be acquired first. Then, an image is reconstructed based on the scanning data of each of the reconstructing points. FIG. 1A is a flowchart illustrating a process of a helical-half-scan method of obtaining scanning data of a reconstructing point according to an example of the present disclosure. The process may include the following steps 101-102.

At step 101, when a condition of a helical-half-scan is satisfied, an initial angle and a final angle of an X-ray tube and a pitch value are determined, where the helical-half-scan refers to a helical scan in which the X-ray tube emits X-rays between the initial angle and the final angle during one circle of rotation of a gantry. A plane of rotation of the gantry may be an X-Y plane. A subject travelling direction may be a Z-direction and be perpendicular to the X-Y plane. In some cases, the pitch value is defined as a ratio between moving distance of the scanning bed during one circle of rotation of the gantry and a width of a collimator in the CT device.

The condition of the helical-half-scan can include that the X-ray tube emits X-rays only at some continuous angles during one circle of rotation of the gantry of the CT device. In some cases, when the detected region of the subject includes a skip region without X-ray radiation, the helical scan satisfies the condition of the helical-half-scan. In some cases, a dual-energy scan satisfies the condition of the helical-half-scan.

In some implementations, the initial angle and the final angle of the X-ray tube are determined according to a preset angle threshold. It is noted that when an absolute value of a difference between the initial angle and the final angle is no less than (equal to or greater than) the preset angle threshold, the obtained scanning data during one circle of rotation of the gantry is sufficient for reconstructing an image. For examples, the preset angle threshold can be a sum of a sector angle $\varphi$ of a detector of a CT device and an angle $\pi$, and minimum scanning data for reconstructing a CT image is scanning data obtained in a case that the absolute value of the difference between the initial angle and the final angle is equal to the preset angle threshold.

The initial angle refers to an included angle between a central axis of a cone-shaped X-ray beam emitted by the X-ray tube and a forward direction of a Y-axis. The final angle refers to an included angle between the central axis of the cone-shaped X-ray beam emitted by the X-ray tube and the forward direction of the Y-axis. It is noted that a plane of rotation of the gantry is an X-Y plane. A travelling direction of the scanning bed is the Z-direction and is perpendicular to the X-Y plane.

In an example, when an included angle between the central axis of the cone-shaped X-ray beam emitted by the X-ray tube and the forward direction of the Y-axis is the initial angle, the X-ray tube begins emitting X-rays; and when the included angle between the central axis of the cone-shaped X-ray beam emitted by the X-ray tube and the forward direction of the Y-axis is the final angle, the X-ray tube stops emitting X-rays.

In some examples, the skip region without X-ray radiation includes: some organs of a human body, such as eyes, an injured region, and the like. For example, when a head of the human body is scanned, it is desired to protect eyes to avoid eye injury due to direct exposure to X-rays. In this case, the X-ray tube of the CT device does not emit X-rays when the X-ray tube rotates to a position over the eyes, and emits X-rays when the X-ray tube rotates to other positions relative to the head.

In some examples, the X-ray tube emits X-rays with high energy and X-rays with low energy for scanning a subject in the dual-energy scan. In this way, different tissues having a similar density may be distinguished according to a CT value and the characteristic of nonlinear attenuation of X-ray energy. In the dual-energy scan, X-rays with high energy may be switched to X-rays with low energy, and X-rays with low energy may also be switched to X-rays with high energy. This energy switching process costs some time in which the X-ray tube does not emit X-rays.

As can be seen, the dual-energy scan satisfies the helical-half-scan condition. When a dual-energy scan is performed, the X-ray tube may emit X-rays only at some continuous angles during one circle of rotation of the gantry of the CT device. In an example, to ensure that an image of any z-position (a z-position is a position of the detected region of the subject in the z-direction) can be reconstructed during the helical-half-scan, it is desired to determine scanning parameters for the helical-half-scan: a pitch value and the initial angle and the final angle of an X-ray tube.

In an example, an image of any z-position can be reconstructed according to the determined pitch value of the helical-half-scan; and scanning data obtained during one circle of rotation of the gantry is sufficient for reconstructing the image of the z-position according to the determined initial angle and final angle of the X-ray tube.

At step 102, scanning data of each of reconstructing points in a reconstructing position is obtained by performing the helical-half-scan on the detected region of the subject based on the initial angle and the final angle of an X-ray tube and the pitch value. The reconstruction position can refer to a z-position.

Figure 1B:
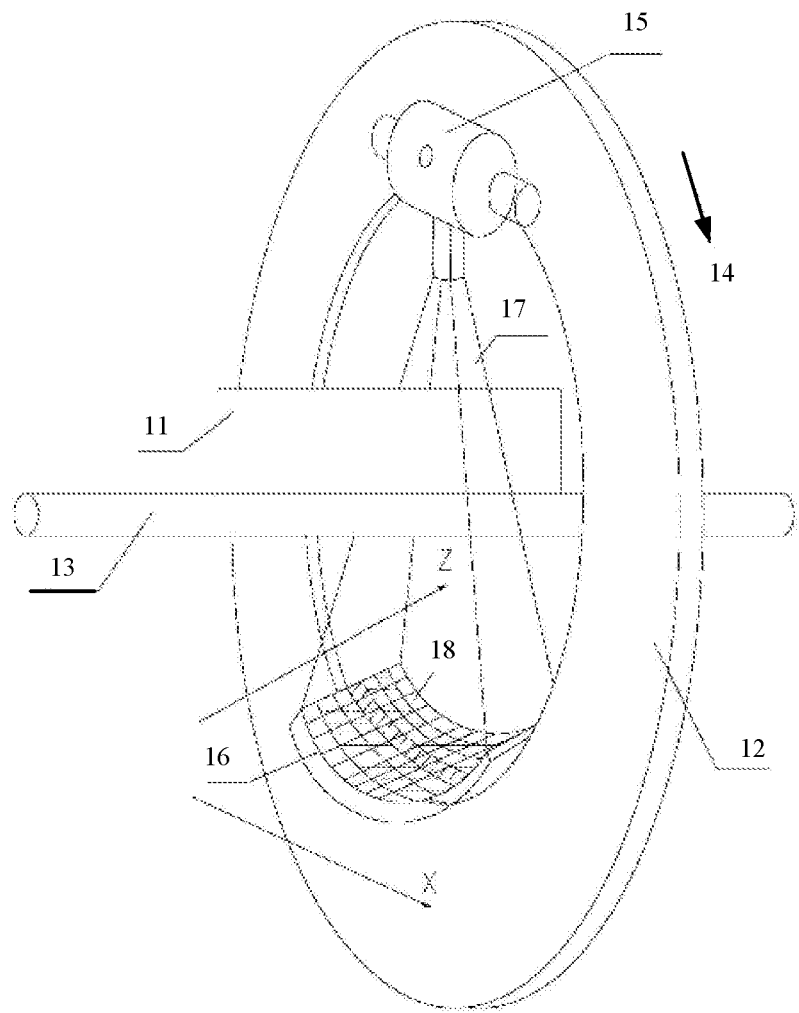
FIG. 1B is a schematic diagram illustrating an application scenario of the method shown in FIG. 1A, according to an example of the present disclosure.

In an application scenario according to an example, as shown in FIG. 1B, when a subject 11, such as a patient is scanned with the CT device, a gantry 12 may rotate around a rotation axis 13 in a clockwise direction indicated by an arrow 14. An X-ray tube 15 and a detector 16 in the gantry 12 may also rotate in the clockwise direction. The cone-shaped X-ray beam 17 emitted by the X-ray tube 15 may penetrate through the subject 11 and then be received by the detector 16. In this way, scanning data of each of reconstructing points in each of reconstructing positions can be obtained. In an example, when it is desired to protect the eyes of the patient, the X-ray tube 15 in the gantry 12 does not emit X-rays when rotating over the eyes of the patient.

As can be seen from the above examples, by using the helical-half-scan method in the present disclosure, the X-ray tube can be controlled to emit X-rays only at some angles during the rotation of the gantry. In this way, under the condition that the CT image of the reconstructing position is reconstructed, some parts of the detected region can be protected, some particular applications can be satisfied, and the scan dose can be saved.

Figure 2A:
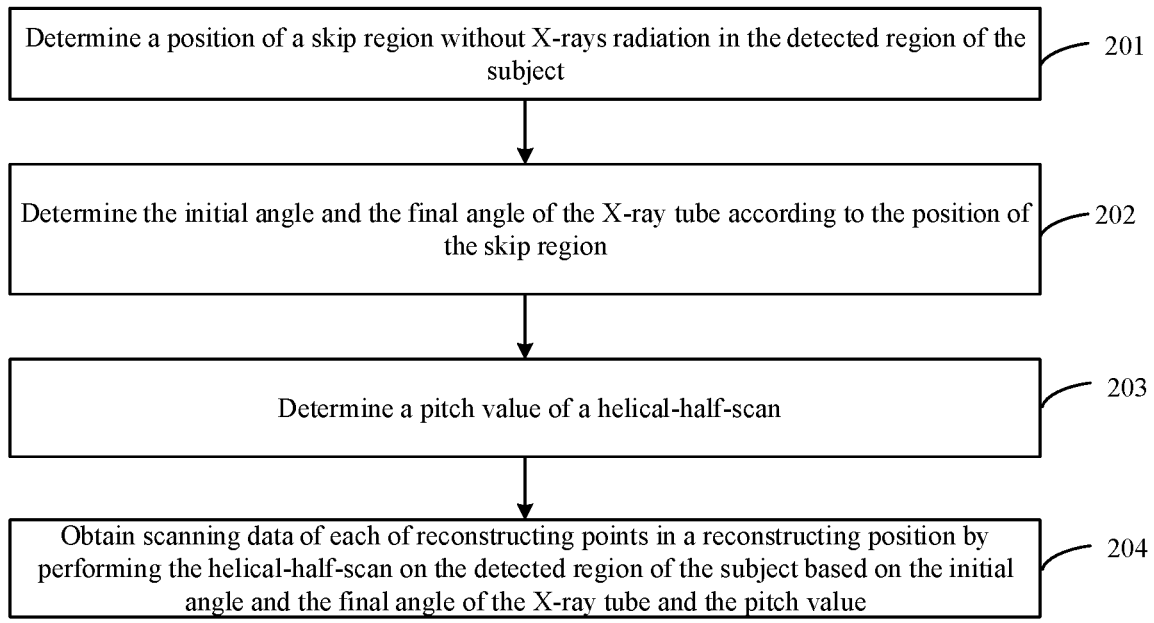
FIG. 2A is a flowchart illustrating a process of a helical-half-scan method of obtaining scanning data of a reconstructing point, according to another example of the present disclosure.

FIG. 2A is a flowchart illustrating a process of a helical-half-scan method of obtaining scanning data of a reconstructing point according to another example of the present disclosure. Under the condition that the detected region of the subject includes a skip region without X-ray radiation, the process may include the following steps 201-204.

At step 201, a position of a skip region without X-rays radiation in the detected region of the subject is determined.

For ease of understanding, parameters involved in this example will be introduced first below.

A full scan refers to a scan in which the X-ray tube emits X-rays during one circle of rotation (e.g., 360 degrees) of the gantry. Compared with the full scan, a half scan refers to a scan in which the X-ray tube emits X-rays only at some continuous angles during one circle of rotation (e.g., 360 degrees) of the gantry, that is, some angles are skipped not to perform ray-emitting scan.

In an example, an operator inputs position parameters corresponding to the position of the skip region to the CT device so that the CT device can determine the position of the skip region according to the position parameters. In an example, when the subject is a patient, the CT device determines the position of the skip region of the patient according to a lying posture of the patient. Then, the CT device may determine an initial angle $\beta_1$ and a final angle $\beta_2$ of the X-ray tube in the present helical-half-scan according to the position of the skip region. When the included angle between the central axis of the cone-shaped X-ray beam emitted by the X-ray tube and the forward direction of the Y-axis is between an interval $[\beta_1, \beta_2]$, the X-ray tube emits X-rays.

For example, when the subject is a patient and the patient lies flat on a scanning bed, if the skip region without X-ray radiation is eyes, the position of the eyes is determined according to the lying posture of the patient. Then, the initial angle $\beta_1$ and the final angle $\beta_2$ of the X-ray tube are determined according to the position of the eyes. In this way, the X-ray tube will not emit X-rays when rotating over the position of the eyes and begins emitting X-rays after rotating over the position of eyes.

At step 202, the initial angle and the final angle of the X-ray tube are determined according to the position of the skip region, where the absolute value of the difference between the initial angle and the final angle of the X-ray tube is equal to or greater than the preset angle threshold.

It is noted that when the absolute value of the difference between the initial angle and the final angle of the X-ray tube is equal to or greater than the angle threshold, the obtained scanning data is sufficient for reconstructing the CT image. The preset angle threshold can be a sum of the sector angle $\varphi$ of the detector of the CT device and the angle $\pi$.

It is further noted that for various CT device with different types and models, the preset angle threshold is set according to the sector angle of the detector of the particular CT device.

In an example, if the absolute value of the angle difference between the initial angle and the final angle of the X-ray tube is lower than the preset angle threshold, it indicates that the obtained scanning data may not be sufficient for reconstructing the CT image. In this case, the operator may be prompted to adjust the initial angle and the final angle of the X-ray tube, such that the absolute value of the angle difference between the adjusted initial angle and the adjusted final angle of the X-ray tube is equal to or greater than the preset angle threshold.

At step 203, a pitch value of a helical-half-scan is determined.

In a full scan, since the X-ray tube emits X-rays during one circle of rotation of the gantry, the obtained scanning data is sufficient so that an image of any z-position can be reconstructed. In a half scan, the X-ray tube emits X-rays only at some continuous angles during one circle of rotation of the gantry, and thus the obtained scanning data is relatively less. In this case, to ensure that an image of any z-position can be reconstructed, an appropriate pitch value for the helical-half-scan can be determined.

In an example, to determine a pitch value of the present helical-half-scan, a maximum pitch value satisfying a condition that an image of any reconstructing position (e.g., Z-position) can be reconstructed can be first obtained according to a reconstructing field of view of the CT device, a radius of rotation of the X-ray tube, a number of slices of the detector, a single-slice thickness of the detector, etc. Then, a value less than the maximum pitch value may be determined as the pitch value of the helical-half-scan.

According to the reconstructing field of view of the CT device, the radius of rotation of the X-ray tube, the number of slices of the detector and the single-slice thickness of the detector, the pitch value p of the helical-half-scan may be determined based on the following formulas (1)-(3):

$$p1(\varphi) = \left( -\frac{midSlice * S * \left( \sqrt{R_F^2 - (R_{FOV} * \cos(\varphi))} - R_{FOV} * \sin(\varphi) \right)}{R_F \left( \theta_1 + a\sin\frac{R_{FOV} * \cos(\varphi)}{R_F} \right)} \right) * \frac{2\pi}{nSlice * S}, \quad (1)$$

$$p2(\varphi) = \left( -\frac{midSlice * S * \left( \sqrt{R_F^2 - (R_{FOV} * \cos(\varphi))} - R_{FOV} * \sin(\varphi) \right)}{R_F \left( \theta_2 + a\sin\frac{R_{FOV} * \cos(\varphi)}{R_F} \right)} \right) * \frac{2\pi}{nSlice * S}, \quad (2)$$

and $$p = \min_{0 \le \varphi \le 2\pi} \min(p1(\varphi), p2(\varphi)). \quad (3)$$

In the above formulas 1-3, $\varphi$ represents the sector angle of the detector; $midSlice = (nSlice - 1) * 0.5$, where nSlice represents the number of slices of the detector; S represents the single-slice thickness of the detector; $R_{FOV}$ represents a reconstructing field of view; $R_F$ represents the radius of rotation of the X-ray tube; $\theta_1$ and $\theta_2$ indicate a number of circles of rotation of the gantry. In practical application, if $\theta_1 = -\pi$ and $\theta_2 = \pi$, it indicates that the gantry rotates one circle; and if $\theta_1 = -2\pi$ and $\theta_2 = 2\pi$, it indicates that the gantry rotates two circles.

Figure 2B:
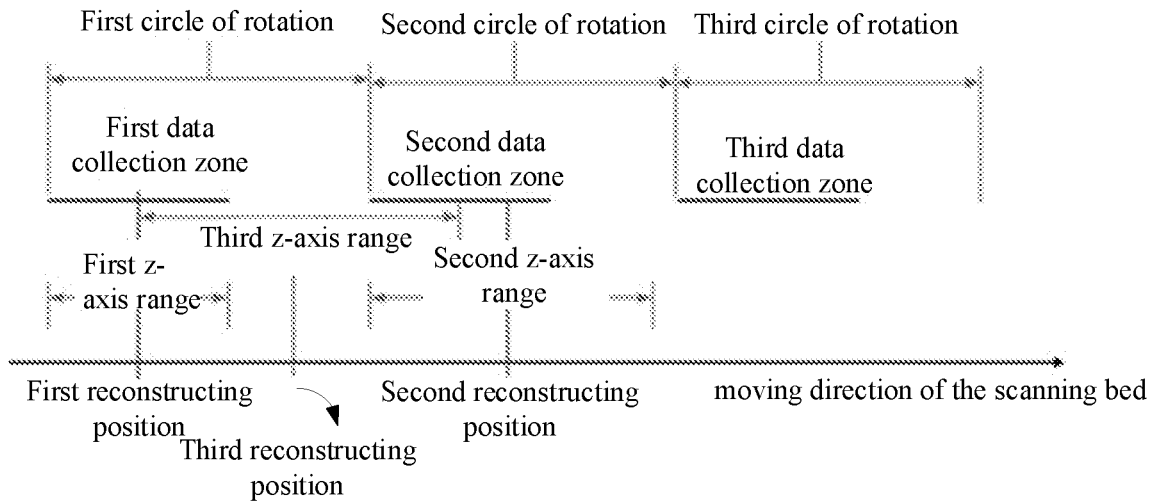
FIG. 2B is a schematic diagram illustrating a relationship between data collection zone and a reconstructing position in a helical-half-scan, according to an example of the present disclosure.

FIG. 2B is a schematic diagram illustrating a relationship between a data collection zone and a reconstructing position in a helical-half-scan according to an example of the present disclosure. In conjunction with an application scenario illustrated in FIG. 2B, how to determine $\theta_1$ and $\theta_2$ in the formulas (1)-(2) is described. As shown in FIG. 2B, it is assumed that the obtained scanning data during one circle of rotation of the gantry is the minimum scanning data for reconstructing an image, for example, when the absolute value of the difference between the initial angle and the final angle of the X-ray tube is the preset angle threshold a, the obtained scanning data during one circle of rotation of the gantry is the minimum scanning data for reconstructing an image. It is understood that if the absolute value of the difference between the initial angle and the final angle of the X-ray tube is greater than the preset angle threshold in the rotation process of the gantry, or the pitch value is less than the maximum pitch value, the obtained scanning data during one circle of rotation of the gantry may be more than the scanning data for reconstructing an image.

As shown in FIG. 2B, the gantry rotates by three circles continuously. The X-ray tube emits X-rays only in a first data collection zone during the first circle of rotation of the gantry. The X-ray tube emits X-rays only in a second data collection zone during the second circle of rotation of the gantry. The X-ray tube emits X-rays only in a third data collection zone during the third circle of rotation of the gantry. It is assumed that in the above three circles of rotation, the absolute value of the difference between the initial angle and the final angle during each of the three circles of rotation of the gantry is same and equal to the present angle threshold a.

As can be seen from FIG. 2B, different reconstructing positions may involve different z-axis ranges. As shown in FIG. 2B, three cases are illustrated. A horizontal axis in FIG. 2B represents a moving direction of the scanning bed, which is parallel with the z-axis.

A first reconstructing position is located within the first data collection zone. In this case, the z-axis range involved by the first reconstructing position begins from a z-position corresponding to the initial angle to a z-position corresponding to the final angle. Thus, the z-axis range involved by the first reconstructing position may be equivalent to a movable range of the scanning bed corresponding to a rotation angle a of the gantry. In FIG. 2B, the z-axis range involved by the first reconstructing position may be referred to as a first z-axis range.

A third reconstructing position is located between the first data collection zone and the second data collection zone. In this case, the obtained scanning data during the first circle of rotation of the gantry may be insufficient for reconstructing an image of the third reconstructing position, and thus a half of the obtained scanning data during the second circle of rotation of the gantry may be added. Thus, as shown in FIG. 2B, the z-axis range involved by the third reconstructing position is: a z-axis range corresponding to the first circle of rotation of the gantry minus a half of a z-axis range corresponding to the first data collection zone and plus a half of a z-axis range corresponding to the second data collection zone. As described above, the first data collection zone and the second data collection zone both correspond to the preset angle threshold a. Thus, the z-axis range involved by the third reconstructing position may be equivalent to a movable range of the scanning bed corresponding to one circle of rotation of the gantry. In FIG. 2B, the z-axis range involved by the third reconstructing position may be referred to as a third z-axis range.

The z-axis range involved by the first reconstructing position and the z-axis range involved by the third reconstructing position are two extreme cases. Apart from the above two extreme cases, the z-axis range involved by the second reconstructing position (referred to as a second z-axis range in FIG. 2B) is greater than the z-axis range involved by the first reconstructing position and smaller than the z-axis range involved by the third reconstructing position. It is understood from the above description that if an image of the third reconstructing position can be reconstructed, an image of other reconstructing positions can be reconstructed. Thus, $\theta_1$ and $\theta_2$ may be determined according to the z-axis range involved by the third reconstructing position. Since the z-axis range involved by the third reconstructing position is a movable range of the scanning bed corresponding to one circle of rotation of the gantry, it is determined that $\theta_1=-\pi$ and $\theta_2=\pi$. $\theta_1=-\pi$ and $\theta_2=\pi$ are substituted into the formula (1) and the formula (2) to obtain the maximum pitch value.

It is noted that since the maximum pitch value determined by the above formulas (1)-(2) is obtained on the basis that the absolute value of the difference between the initial angle and the final angle of the X-ray tube in one helical-half-scan is the preset angle threshold, an image of any reconstructing position can be reconstructed in a case that the pitch value is less than the maximum pitch value.

In an example, a pitch value of the present helical-half-scan is input by an operator. If the pitch value input by the operator is less than the maximum pitch value, the pitch value input by the operator is taken as the pitch value of the present helical-half-scan. If the pitch value input by the operator is no less than the maximum pitch value, a pitch value less than the maximum pitch value may be automatically selected by the CT device as the pitch value of the present helical-half-scan. In some cases, if the pitch value input by the operator is no less than the maximum pitch value, the operator may be prompted to adjust the pitch value, such that the pitch value is less than the maximum pitch value.

At step 204, scanning data of each of reconstructing points in a reconstructing position is obtained by performing the helical-half-scan on the detected region of the subject based on the initial angle and the final angle of the X-ray tube and the pitch value.

As can be seen from the above examples, when some parts of the detected region of the subject need to be protected in the helical scan, the X-ray tube may be set not to emit X-rays when rotating over such parts and emit X-rays when rotating after such parts. In this way, under the condition that the CT image of the reconstructing position is reconstructed, some parts of the detected region can be protected, some particular applications can be satisfied, and the scan dose can be saved.

Figure 3A:
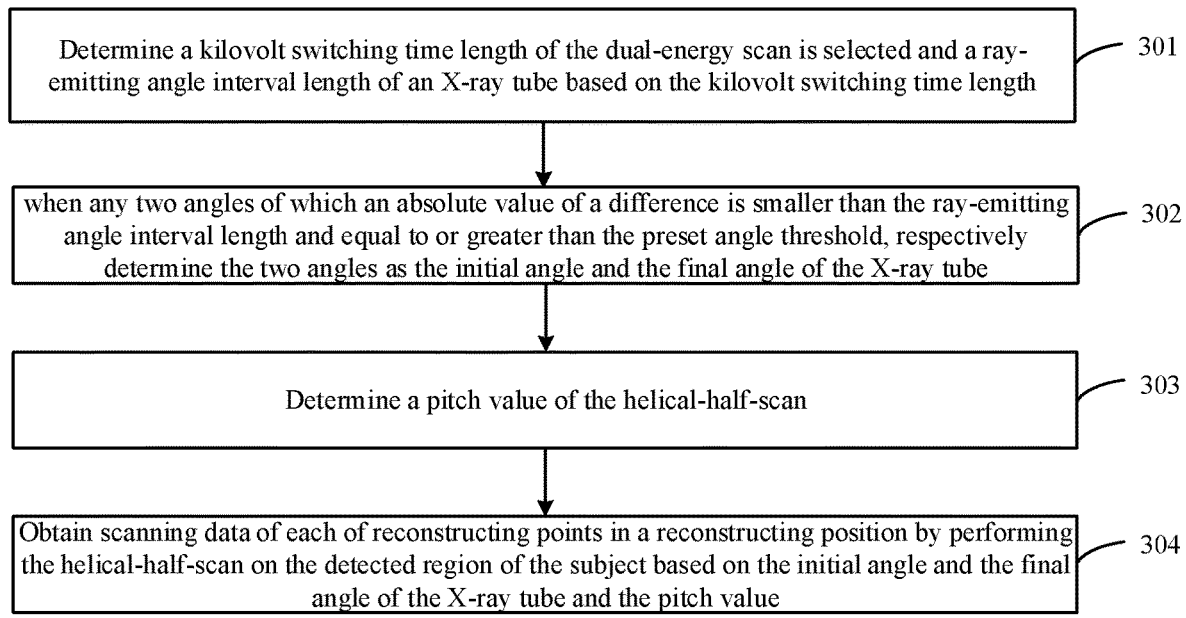
FIG. 3A is a flowchart illustrating a process of a helical-half-scan method of obtaining scanning data of a reconstructing point, according to still another example of the present disclosure.

FIG. 3A is a flowchart illustrating a process of a helical-half-scan method of obtaining scanning data of a reconstructing point according to still another example of the present disclosure. The method is applied to the dual-energy scan. The process may include the following steps 301-304.

At step 301, a kilovolt (KV) switching time length of the dual-energy scan is selected and a ray-emitting angle interval length of an X-ray tube is determined based on the kilovolt switching time length.

Figure 3B:
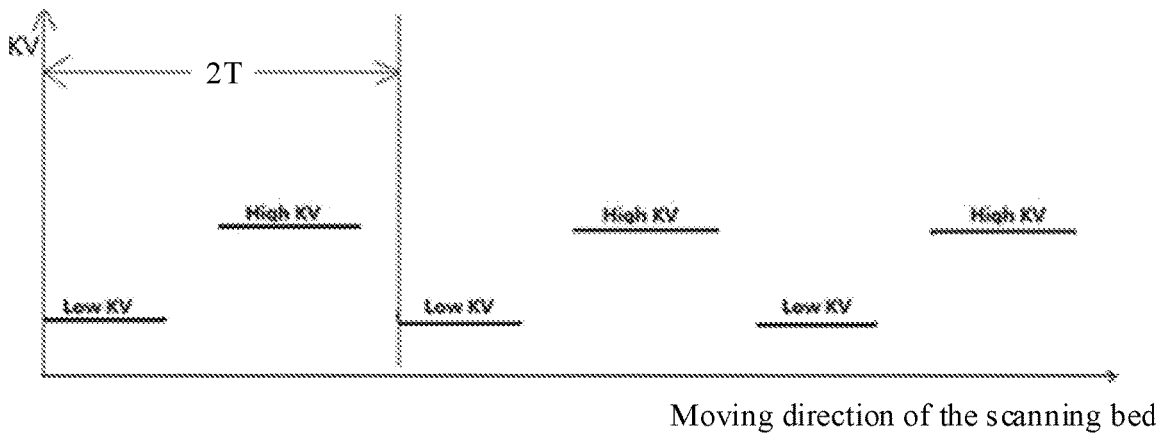
FIG. 3B is a schematic diagram illustrating switching between high energy and low energy in a dual-energy scan, according to an example of the present disclosure.
Figure 3C:
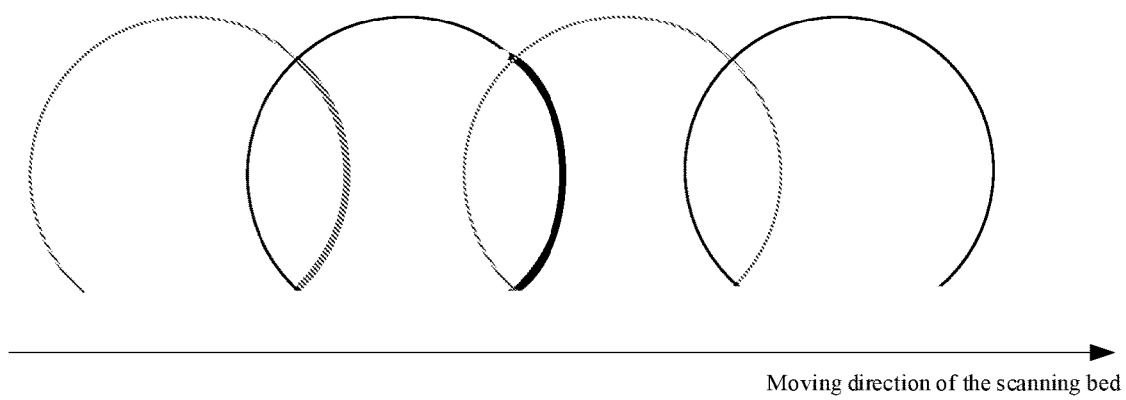
FIG. 3C is a schematic diagram illustrating a dual-energy scan, according to an example of the present disclosure.

FIG. 3B is a schematic diagram illustrating switching between high energy and low energy of a dual-energy scan according to an example. FIG. 3C is a schematic diagram illustrating a dual-energy scan according to an example. For ease of understanding, the dual-energy scan will be introduced in conjunction with FIG. 3B and FIG. 3C. As shown in FIG. 3B, T represents a time length of one circle of rotation of the gantry; Low KV represents low energy used in the dual-energy scan and High KV represents high energy used in the dual-energy scan. The switching time length between high energy and lower energy is the kilovolt switching time length KVSwitch of the dual-energy scan. As shown in FIG. 3C, a first arc corresponds to a Low KV scan in FIG. 3B, a second arc corresponds to a High KV scan in FIG. 3B, and a thick line segment of the first arc represents the switching from low energy to high energy and a thick line segment of the second circle represents the switching from high energy to low energy.

In an example, since the X-ray tube does not emit X-rays in the energy switching process and the switching time length is KVSwitch, the ray-emitting time length of the X-ray tube is T−KVSwitch. The ray-emitting angle interval length of the X-ray tube can be determined according to the ray-emitting time length T−KVSwitch and the time length T of one circle of rotation of the gantry.

A formula (4) for determining the ray-emitting angle interval length $\beta_3$ of the X-ray tube is shown as below:

$$\beta_3 = \frac{T - KVSwitch}{T} * 2 * \pi. \tag{4}$$

At step 302, when any two angles of which an absolute value of a difference is smaller than the ray-emitting angle interval length and equal to or greater than the preset angle threshold, the two angles are respectively determined as the initial angle and the final angle of the X-ray tube.

To make the obtained scanning data be sufficient for reconstructing an image, the absolute value of the difference between the initial angle and the final angle is greater than or equal to the preset angle threshold. Since the time at which the energy switching occurs is not limited in the dual-energy scan, if the ray-emitting angle interval length is equal to or greater than the preset angle threshold, any two angles of which the absolute value of the difference equal to or greater than the preset angle threshold and smaller than the ray-emitting angle interval length may be respectively determined as the initial angle and the final angle of the X-ray tube in the helical-half-scan.

In an example, if the ray-emitting angle interval length is smaller than the preset angle threshold, it indicates that the obtained scanning data is insufficient for reconstructing a CT image, and in this case, an operator may be prompted to adjust the energy switching time length, such that the adjusted ray-emitting angle interval length is not smaller than the preset angle threshold.

At step 303, a pitch value of the helical-half-scan is determined.

As described above, to ensure that an image of any z-position can be reconstructed, an appropriate pitch value for the helical-half-scan can be determined.

When the helical-half-scan is a dual-energy scan, the manner of determining the pitch value of the helical-half-scan is the same as in step 203, and thus is not described in detail here again.

Figure 3D:
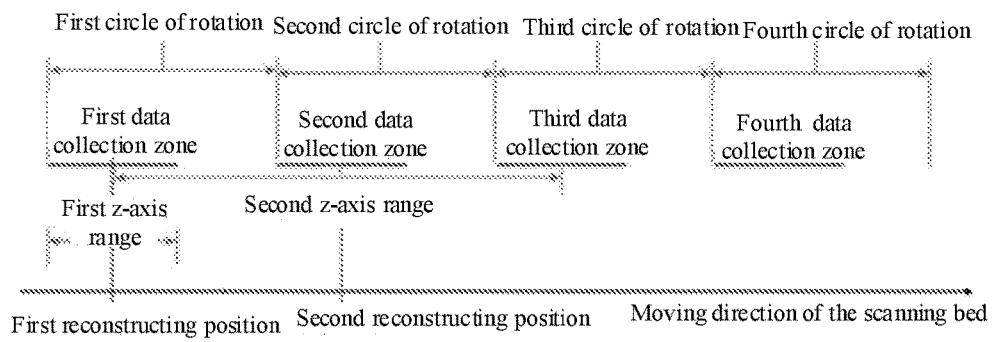
FIG. 3D is a schematic diagram illustrating a relationship between data collection zone and a reconstructing position in a dual-energy scan in a dual-energy scan, according to an example of the present disclosure.

FIG. 3D is a schematic diagram illustrating a relationship between data collection zone and a reconstructing position in a dual-energy scan according to an example of the present disclosure. In conjunction with an application scenario illustrated in FIG. 3D, how to determine $\theta_1$ and $\theta_2$ in the formulas (1)-(2) is described. As shown in FIG. 3D, it is assumed that the obtained scanning data during one circle of rotation of the gantry is the minimum scanning data for reconstructing an image, for example, when the absolute value of the difference between the initial angle and the final angle of the X-ray tube is the preset angle threshold a, the obtained scanning data during one circle of rotation of the gantry is the minimum scanning data for reconstructing an image.

As shown in FIG. 3D, the gantry rotates by four circles continuously. The X-ray tube emits X-rays, such as high energy X-rays, only in the first data collection zone during the first circle of rotation of the gantry. The X-ray tube emits X-rays, such as low energy X-rays only in the second data collection zone during the second circle of rotation of the gantry. The X-ray tube emits X rays, such as high energy X-rays only in the third data collection zone during the third circle of rotation of the gantry. The X-ray tube emits X-rays, such as low energy X-rays only in the fourth data collection zone during the fourth circle of rotation of the gantry. It is assumed that in the above four circles of rotation, the absolute value of the difference between the initial angle and the final angle during each of the four circles of rotation of the gantry is same and equal to the present angle threshold a.

In the dual-energy scan, scanning data in adjacent data collection zones is obtained by using X-rays of two different energy levels and thus cannot be used together for reconstructing an image of a reconstructing position (a z-position). The scanning data obtained by X-rays of the same energy level may be used to reconstruct the image of the reconstructing position, that is, the scanning data obtained every other data collection zones can be used together for reconstructing an image.

As can be seen from FIG. 3D, different reconstructing positions may involve different z-axis ranges. As shown in FIG. 3D, two cases are illustrated. A horizontal axis in FIG. 3D represents a moving direction of the scanning bed, which is parallel with the z-axis.

A first reconstructing position is located within the first data collection zone. In this case, the z-axis range involved by the first reconstructing position begins from a z-position corresponding to the initial angle to a z-position corresponding to the final angle. Thus, the z-axis range involved by the first reconstructing position may be equivalent to a movable range of the scanning bed corresponding to a rotation angle a of the gantry. In FIG. 3D, the z-axis range involved by the first reconstructing position may be referred to as a first z-axis range.

A second reconstructing position is located between the first data collection zone and the third data collection zone. In this case, the obtained scanning data during the first circle of rotation of the gantry may be insufficient for reconstructing an image of the second reconstructing position, and thus the obtained scanning data during the second circle of rotation of the gantry and a half of the obtained scanning data during the third circle of rotation of the gantry may be added. Thus, as shown in FIG. 3D, the z-axis range involved by the second reconstructing position is: a z-axis range corresponding to the first circle of rotation of the gantry minus a half of a z-axis range corresponding to the first data collection zone plus a z-axis range corresponding to the second circle of rotation of the gantry plus a half of a z-axis range corresponding to the third data collection zone. As described above, the first data collection zone, the second data collection zone and the third data collection zone all correspond to the preset angle threshold a. Therefore, the z-axis range involved by the second reconstructing position may be equivalent to a movable range of the scanning bed corresponding to two circles of rotation of the gantry. In FIG. 3D, the z-axis range involved by the second reconstructing position may be referred to as a second z-axis range. Also, the second z-axis range includes scanning data from adjacent data collections zones obtained by using X-rays of two different energy levels. As discussed below, the scanning data with the same energy level can be first separated before being used to reconstruct the image at the second reconstruction position.

From the above description, it is understood that if an image of the second reconstructing position can be reconstructed, an image of other reconstructing positions can be reconstructed. Thus, $\theta_1$ and $\theta_2$ may be determined according to the z-axis range involved by the second reconstructing position. Since the z-axis range involved by the second reconstructing position is the movable range of the scanning bed corresponding to two circles of rotation of the gantry, it may be determined that $\theta_1=-2\pi$ and $\theta_2=2\pi$. $\theta_1=-2\pi$ and $\theta_2=2\pi$ are substituted into the formula (1) and the formula (2) to obtain the maximum pitch value.

It is noted that since the maximum pitch value determined by the above formulas (1)-(2) is obtained on the basis that the absolute value of the difference between the initial angle and the final angle of the X-ray tube in one helical-half-scan is the preset angle threshold, an image of any reconstructing position can be reconstructed in a case that the pitch value is less than the maximum pitch value.

In an example, the pitch value of the present helical-half-scan is input by the operator. If the pitch value input by the operator is less than the maximum pitch value, the pitch value input by the operator is taken as the pitch value of the present helical-half-scan. If the pitch value input by the operator is not less than the maximum pitch value, a pitch value less than the maximum pitch value may be automatically selected by the CT device as the pitch value of the present helical-half-scan. In some cases, if the pitch value input by the operator is no less than the maximum pitch value, the operator may be prompted to adjust the pitch value, such that the pitch value is less than the maximum pitch value.

At step 304, scanning data of each of reconstructing points in a reconstructing position is obtained by performing the helical-half-scan on the detected region of the subject based on the initial angle and the final angle of the X-ray tube and the pitch value.

As can be seen from the above examples, in the helical-half-scan method provided by the present disclosure, when the present scan is the dual-energy scan, the appropriate initial angle and the final angle of the X-ray tube and a pitch value can be set, so that an image of each of reconstructing positions in the dual-energy scan can be reconstructed.

Apart from the above application scenarios, the helical-half-scan method provided by the present disclosure may also be applied to some scenarios in which the time resolution is limited. For example, when a heart is to be scanned, to ensure the quality of a reconstructed image, the initial angle and the final angle of the X-ray tube are determined in conjunction with a state of motion of the heart. In an example, the heart is scanned in a time length in which the heart moves relatively slowly. At this time, the time length in which the heart moves relatively slowly may be determined according to an electrocardiogram. In addition, the pitch value may be determined according to the determining manner illustrated in FIG. 2A, which will not be redundantly described herein.

Before introducing a method of reconstructing an image according to an example of the present disclosure, for ease of understanding, parameters involved in the helical-half-scan and an image reconstruction process will be explained in conjunction with FIG. 1B: a sampling view, a channel position and a slice position. One circle of rotation of the gantry 12 includes a certain quantity of sampling views. A sampling view corresponds to a sampling angle that is defined as an included angle between the central axis of the cone-shaped X-ray beam emitted by the X-ray tube and the forward direction of the Y-axis. A plane of rotation of the gantry may be an X-Y plane. A subject travelling direction may be a Z-direction and be perpendicular to the X-Y plane.

During the helical-half-scan, a plurality of sampling views may be obtained. With the rotation of the gantry 12, the scanning bed carrying the subject 11 moves along the Z-axis direction, such that each of the plurality of sampling views correspond to a z-position (a reconstructing position) in the rotation process of the gantry 12. The z-position may be a z-axis coordinate of an intersection point at which the central axis of the cone-shaped rays beam for the sampling view intersects the rotation axis 13 of the gantry 12. It is noted that not each of the sampling views contains a reconstructing point in its coverage. A coverage of the sampling view refers to a cone-shaped range formed by the cone-shaped rays 17 emitted by the X-ray tube 15. Part of the rays within the coverage may penetrate through the detected region of the subject 11 and this part of rays can be received by a detector 16 after penetrating through the detected region so as to obtain scanning data.

The detector 16 shown in FIG. 1B is a multi-slice detector, which includes a plurality of two-dimensional detector unit array in X-direction and Z-direction shown in FIG. 1B. The X-direction may be referred to as a channel direction and include a plurality of channel positions. The Z-direction may be referred to as a slice direction and include a plurality of slice positions. For example, the detector unit 18 in FIG. 1B is located in the third channel position and the seventh slice position of the detector. In a rotation process of the gantry, each of the detector units may obtain a set of scanning data.

Figure 4:
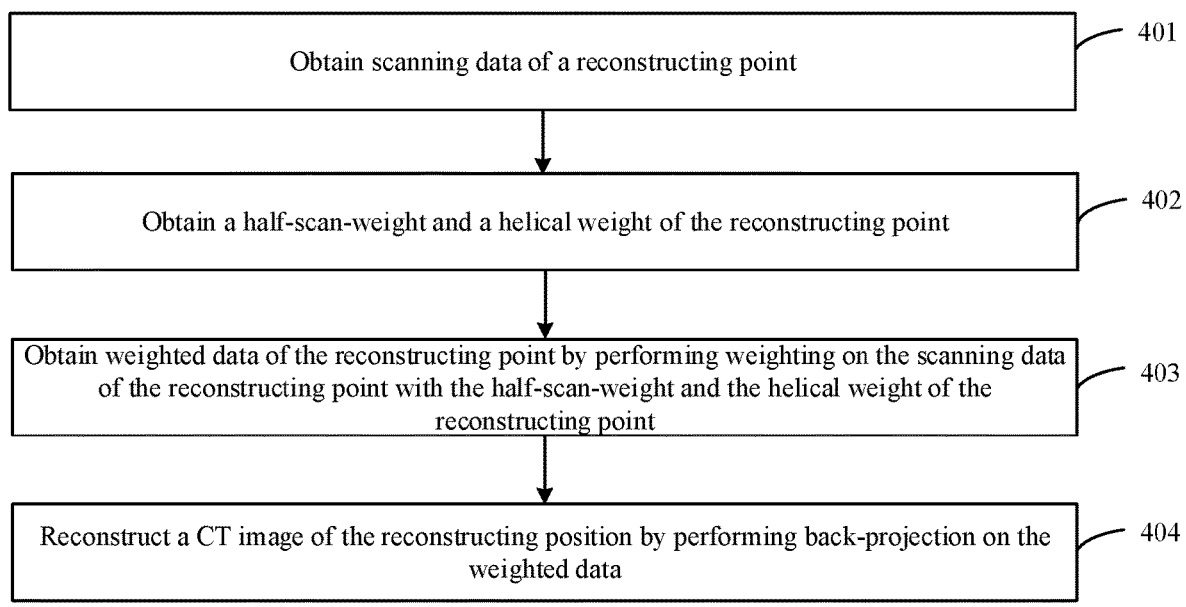
FIG. 4 is a flowchart illustrating a process of a method of reconstructing an image, according to an example of the present disclosure.

FIG. 4 is a flowchart illustrating a process of method of reconstructing an image according to an example of the present disclosure. The method may be used to reconstruct an image with scanning data of each of reconstructing points in a reconstructing position obtained by the above helical-half-scan method. The process may include the following steps.

At step 401, scanning data of a reconstructing point is obtained.

At step 402, a half-scan-weight and a helical weight of the reconstructing point are obtained.

In an example, for each of the reconstructing points, the half-scan-weight and the helical weight of the reconstructing point may be determined by using the sampling angles for all the sampling views within the scanning data corresponding to the reconstructing point.

For example, the half-scan-weight of each of the reconstructing point may be determined according to the following formula (5):

$$x(i, j) = \begin{cases} \frac{1}{\theta_m + 2\gamma_j} * (\theta_i - \theta_m + \gamma_j) & \theta_i < \theta_m + \gamma_j + \gamma_m \\ 1 & \theta_i < \pi + \gamma_j + \gamma_m \\ \frac{1}{2\gamma_j - \theta_m} * (\theta_i + \gamma_j - \gamma_m - (\pi + \theta_m)) & \theta_i < \pi + \gamma_m \\ 0 & \text{else} \end{cases} \quad (5)$$

and $$w_h(i, j) = (3 - 2 * x(i, j)) * x(i, j) * x(i, j).$$

Where, j) represents a reference value of the half-scan-weight of the reconstructing point at the i-th View and the j-th channel; $w_h(i, j)$ represents the half-scan-weight of the reconstructing point at the i-th View and the j-th channel; $\theta_m$ represents a half of an angle which is obtained in a way that the absolute value of the difference between the initial angle and the final angle subtracts an angle $\pi$; $\gamma_m$ represents a half of a sector angle of the detector; $\gamma_j$ represents a sector angle corresponding to the j-th channel; and $\theta_i$ represents a sampling angle of the i-th View. It is noted that the sector angle corresponding to the j-th channel represents an included an angle between the j-th channel and the central axis of the cone-shaped X-ray beam emitted by the X-ray tube.

For example, the helical weight of each of the reconstructing points may be determined according to formulas (6)-(9):

$$trans = \begin{cases} 2\pi & \theta_{max} > 4\pi \\ \theta_{max} - 2\pi & \theta_{max} > 2\pi \\ \frac{\theta_{max}}{2} & \text{else} \end{cases} \quad (6)$$

$$topValue = \begin{cases} \frac{2\pi}{\theta_{max} - 2\pi} & \theta_{max} > 4\pi \\ 1 & \text{else} \end{cases} \quad (7)$$

$$w(\theta) = \begin{cases} \frac{topValue}{trans}\theta & 0 < \theta < trans \\ topValue & \theta < \theta_{max} - trans \\ \frac{topValue}{trans}(\theta_{max} - \theta) & \theta < \theta_{max} \\ 0 & \text{else} \end{cases}, \text{ and} \quad (8)$$

$$w(\theta) = \frac{w(\theta)}{\sum_0^k w(\theta_b + i * 2 * \pi)}. \quad (9)$$

Where, trans represents a view range in which a helical weight changes from 0 to topValue, and topValue represents a maximum value of the helical weight of the reconstructing point; $w(\theta)$ represents the helical weight of the reconstructing point when the sampling angle is $\theta$; $\theta_{max}$ represents an angle range corresponding to the scanning data for reconstructing an image; $\theta_b = \text{mod}(\theta, 2\pi)$, $$k = INT\left(\frac{(\theta_b - \theta_{max})}{2\pi}\right),$$

and i represents the i-th view. In addition, the formula (9) may represent that a sum of the helical weights of the reconstructing points corresponding to the sampling angle of a same sampling view is 1.

The determination manners for the half-scan-weight and the helical weight of each of reconstructing points may also be other manners that are well known to those skilled in the art, which will not be limited herein.

The half-scan-weight and the helical weight of each of the reconstructing points are determined according to the above manner, and then weighting may performed on the scanning data of each of the reconstructing points.

At step 403, weighted data of the reconstructing point is obtained by performing weighting on the scanning data of the reconstructing point with the half-scan-weight and the helical weight of the reconstructing point.

A person skilled in the art may employ a well-known weighting manner to weight the scanning data of the reconstructing point, which will not be limited herein.

At step 404, a CT image of the reconstructing position is reconstructed by performing back-projection on the weighted data.

In an example of the present disclosure, the back-projection may be performed on the weighted data according to reconstructing parameters, such as a reconstructing field of view, a reconstructing center, a detected region, an image resolution, a matrix for reconstructing an image and the like, set by the operator, thereby reconstructing an image.

It can be seen from the above examples that an image can be reconstructed with the weighted data.

Figure 5A:
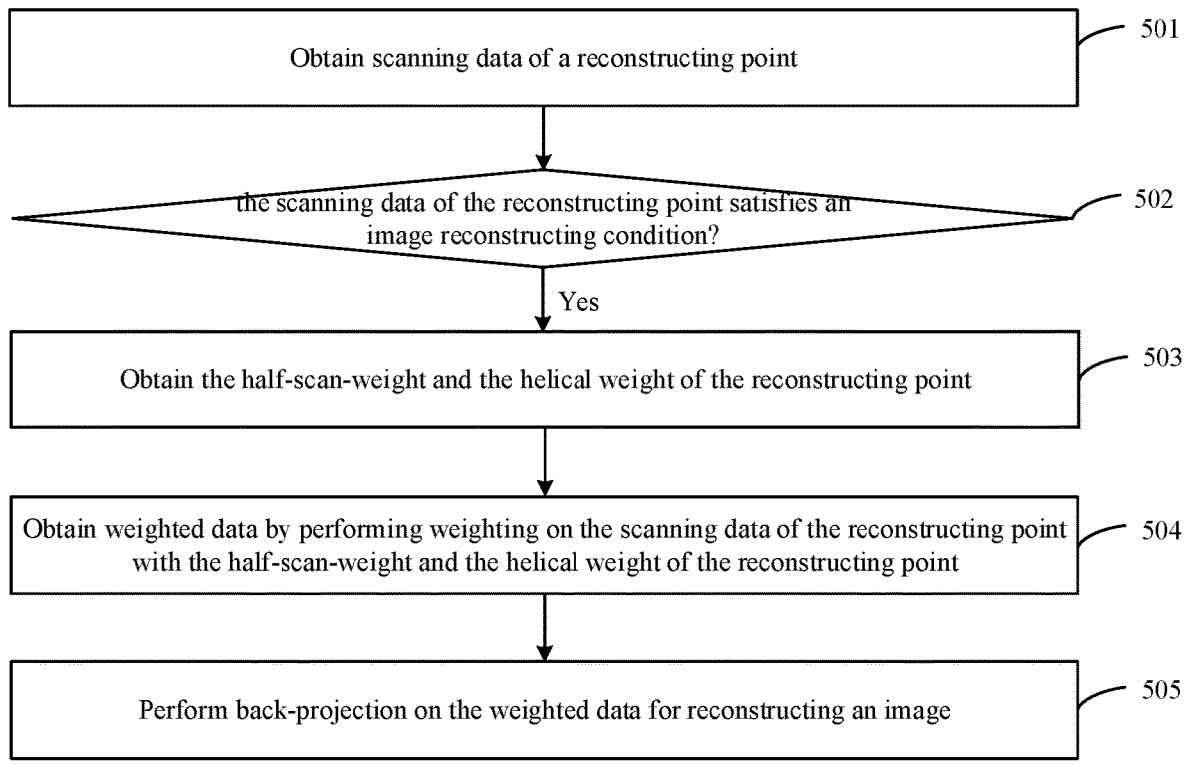
FIGS. 5A-5C are a flowcharts illustrating a method of reconstructing an image, according to another example of the present disclosure.

FIG. 5A is a flowchart illustrating a process of a method of reconstructing an image according to another example of the present disclosure. To make the process more efficient, it may be determined first whether the scanning data of the reconstructing point satisfies an image reconstructing condition, and after the image reconstructing condition is satisfied, weight parameters may be determined. In this case, the process may include the following steps.

At step 501, scanning data of a reconstructing point is obtained.

At step 502, it is determined whether the scanning data of the reconstructing point satisfies an image reconstructing condition, and if yes, step 503 is performed. It is noted that if the scanning data of the reconstructing point does not satisfy the image reconstructing condition, it may indicate that the reconstructing parameters needs to be adjusted.

In an example of the present disclosure, description will be made with a reconstructing point (x, y, z) for example (the processes for a plurality of reconstructing points are similar). First, a data range for reconstructing an image of the reconstructing point is determined from the scanning data of the reconstructing point, where the data range may include a plurality of sampling views, and the coverage of each of the sampling views contains the reconstructing point. Then, it is determined whether the data within the data range satisfies a preset image reconstructing condition.

When the data range is determined, if a slice and a channel corresponding to a sampling view of a z-position pass through the reconstructing point (x, y, z), the coverage of the sampling view contains the reconstructing point (x, y, z), and the scanning data obtained at the sampling view can be used to reconstruct the image of the reconstructing point. A plurality of sampling views are included in the data range for reconstructing the image of the reconstructing point, and by determining the data range, the plurality of sampling views for reconstructing the image of the reconstructing point may be determined. For example, the data range for reconstructing the image of the reconstructing point includes a plurality of sampling views, an absolute range of sampling angles corresponding to the reconstructing point may be $[\theta_{absolutemin}, \theta_{absolutemax}]$, and the number of the sampling views included in the absolute range may be n, where n is an integer greater than or equal to 1.

Figure 5B:
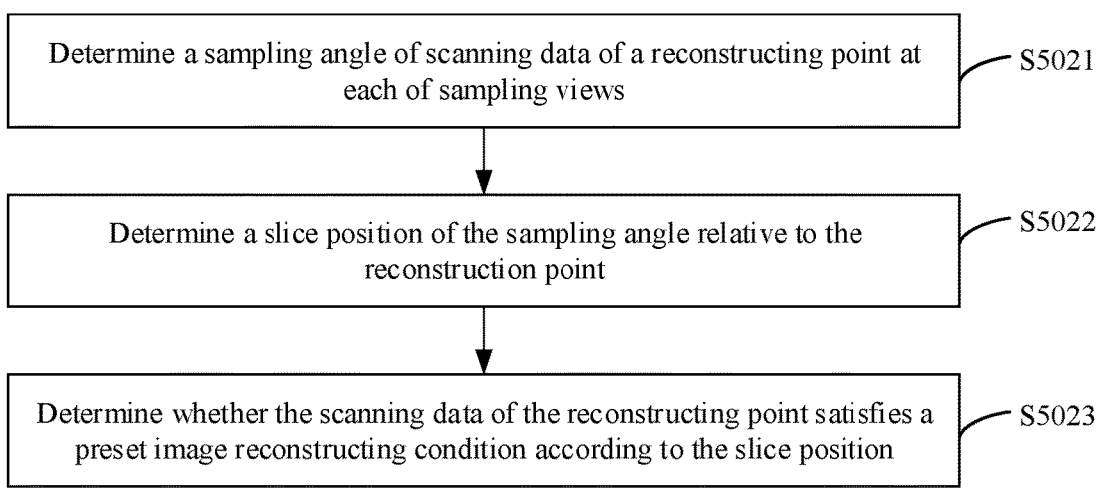

In an example, the scanning data is obtained by performing a helical-half-scan on the subject by using X-rays of one energy level, and in this case, the above step 502 may include sub-steps S5021-S5023, as shown in FIG. 5B.

At sub-step S5021, a sampling angle of the scanning data of the reconstructing point at each of the sampling views is determined.

At sub-step S5022, a slice position of the sampling angle relative to the reconstructing point is determined according to the coordinate of the reconstructing point.

In an example, scanning data obtained during the helical-half-scan is based on a sector beam structure. The scanning data based on the sector beam structure may be converted into scanning data based on a parallel beam structure. For example, for a sampling view under the parallel beam structure, its sampling angle is $\theta_i$ and the slice position of the sampling angle relative to the reconstructing point is $q_i$. The slice position of the sampling angle relative to the reconstructing point may be determined according to the coordinate of the reconstructing point. The determination method of the slice position $q_i$ may be as shown by formulas (10)-(13):

$$t_i = x\cos\theta_i - y\sin\theta_i, \tag{10}$$

$$v_i = y\cos\theta_i + x\sin\theta_i, \tag{11}$$

$$\gamma_i = a\sin\frac{t_i}{R_F}, \text{ and} \tag{12}$$

$$q_i = \frac{R_F\left(z - (\gamma_i + \theta_i)\frac{p*nSlice*S}{2\pi}\right)}{S\left(\sqrt{R_F^2 - t_i^2} - v_i\right)}. \tag{13}$$

Where (x, y, z) represents the coordinate of the reconstructing point; nSlice represents a number of slices of the detector; S represents a single-slice thickness of the detector; $R_F$ represents a radius of rotation of the X-ray tube; and p represents the pitch value.

At sub-step S5023, it is determined whether the scanning data of the reconstructing point satisfies the preset image reconstructing condition according to the slice position of the sampling angle relative to the reconstructing point.

In an example, for the reconstructing point, the number nView of the sampling views satisfying $0 \leq q_i \leq nSlice-1$ may be determined first according to the slice position of each of the sampling angles. The number nView of the sampling views satisfying $0 \leq q_i \leq nSlice-1$ may be defined as a number of valid sampling views (may also be referred to as valid sampling angles) relative to the reconstructing point. Then, it is determined whether the number nView of the valid sampling views is equal to or greater than a preset sampling number threshold $$\left(\text{such as, } \frac{a}{2\pi}*viewPerRot\right).$$

In this way, if the number nView of the valid sampling views of the reconstructing point is equal to or greater than the preset sampling number threshold, it may be determined that the scanning data of the reconstructing point satisfies the preset image reconstructing condition, that is, the scanning data of the reconstructing point can be used to reconstruct the image of the reconstructing position. Here, a represents the preset angle threshold, and the preset angle threshold is a sum of the sector angle φ of the detector of the CT device and the angle π, and viewPerRot represents the number of the sampling views obtained during one circle of rotation of the gantry.

Figure 5C:
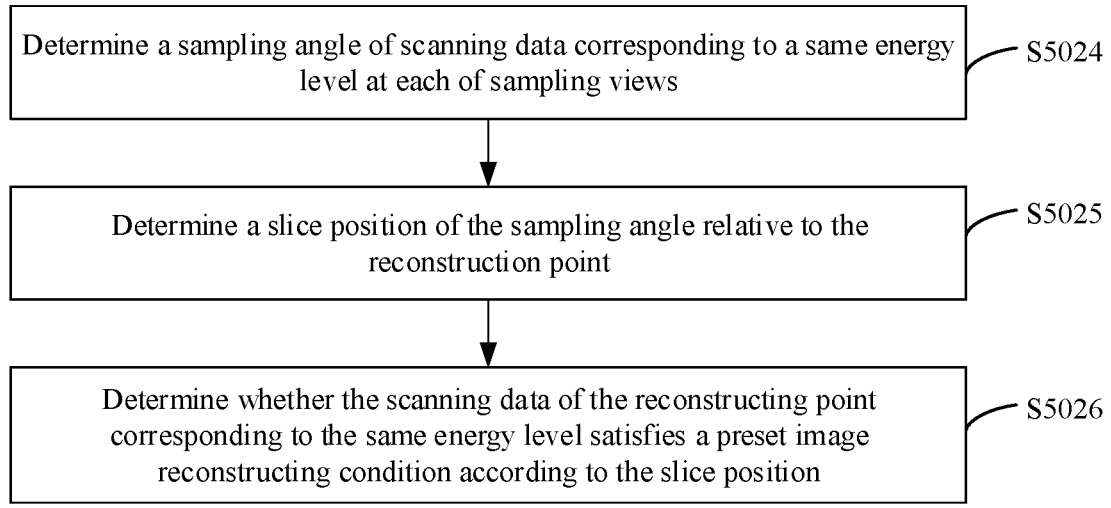

In another example, the scanning data of the reconstructing point is obtained by performing a helical-half-scan on the subject with X-rays of two energy levels. In this case, the above step 502 may include sub-steps S5024-S5026, as shown in FIG. 5C.

At sub-step S5024, for the scanning data of the reconstructing point corresponding to the same energy level, a sampling angle of the scanning data corresponding to the same energy level at each of sampling views is determined.

It is noted that only the scanning data of the reconstructing point corresponding to the same energy level can be used to reconstruct the image of the reconstructing position. The reconstructing point is located on the reconstructing position. In the dual-energy scan, for each of the reconstructing points on the reconstructing position, the scanning data corresponding to high energy and the scanning data corresponding to low energy are first separated from the scanning data of the reconstructing point, and then the scanning data corresponding to high energy and the scanning data corresponding to low energy are respectively processed. The scanning data corresponding to high energy can be used to reconstruct a first image. The scanning data corresponding to low energy can be used to reconstruct a second image. A manner for separating the scanning data corresponding to high energy and the scanning data corresponding to low energy may be any manner that is well known to a person skilled in the art, which is not limited herein.

At sub-step S5025, the slice position of the sampling angle relative to the reconstructing point is determined according to the coordinate of the reconstructing point.

The sub-step S5025 is consistent with the sub-step S5022, which will not be described in detail for the sake of simplicity.

At sub-step S5026, it is determined whether the scanning data of the reconstructing point corresponding to the same energy level satisfies the preset image reconstructing condition according to the slice position of the sampling angle relative to the reconstructing point.

The sub-step S5026 is consistent with the step S5023, which will not be described in detail for the sake of simplicity.

It is noted that the scanning data based on the sector beam structure may be converted into the scanning data based on the parallel beam structure. Therefore, data such as angles, geometrical relationships and the like mentioned in the subsequent image reconstructing steps all are based on the parallel beam structure. In a practical application, any technical approach that is well known to a person skilled in the art for converting CT scanning data from the sector beam structure into the parallel beam structure can be employed, which will not be redundantly described herein.

At step 503, the half-scan-weight and the helical weight of the reconstructing point are obtained.

The step 503 in this example of the present disclosure is similar to the step 402 in the example illustrated in FIG. 4, which is referred to the example illustrated in FIG. 4 and will not be redundantly described herein.

At step 504, weighted data is obtained by performing weighting on the scanning data of the reconstructing point with the half-scan-weight and the helical weight of the reconstructing point.

At step 505, back-projection is performed on the weighted data for reconstructing an image.

In an example of the present disclosure, the back-projection may be performed on the weighted data according to the following formula (14) to reconstruct an image:

$$f(x,y,z)=\Sigma_{i=0}^{nView-1} f^c(\theta_i, t(x,y,z), q(x,y,z))$$ (14).

Where $f^c(\theta_i)$ represents a convolution result of the weighted data $f^w(\theta_i)$; nView represents the number of valid views for reconstructing a reconstructing point; $q(x, y, z)$ represents a slice coordinate under a sampling view; $t(x, y, z)$ represents a channel coordinate under the sampling view.

As can be seen from the above examples, before some weight parameters are determined, it is determined whether the scanning data of the reconstructing point satisfies the image reconstructing condition. After it is determined that the image reconstructing condition is satisfied, some weight parameters are then determined. In this way, the process for reconstructing an image is more efficient.

It should be noted that although in the drawings, steps of the method in the present disclosure are described in a particular sequence, it is not required or implied that these steps must be performed in this particular sequence, or all the shown steps must be performed so as to achieve expected results. Rather, the sequence of the steps depicted in the flowcharts may be changed. Additionally or alternatively, some steps may be omitted, or a plurality of steps may be combined into one step, and/or one step may be split into a plurality of steps.

Corresponding to the examples of the method of reconstructing an image provided in the present disclosure, the present disclosure further provides examples of a device for reconstructing an image.

Figure 6:
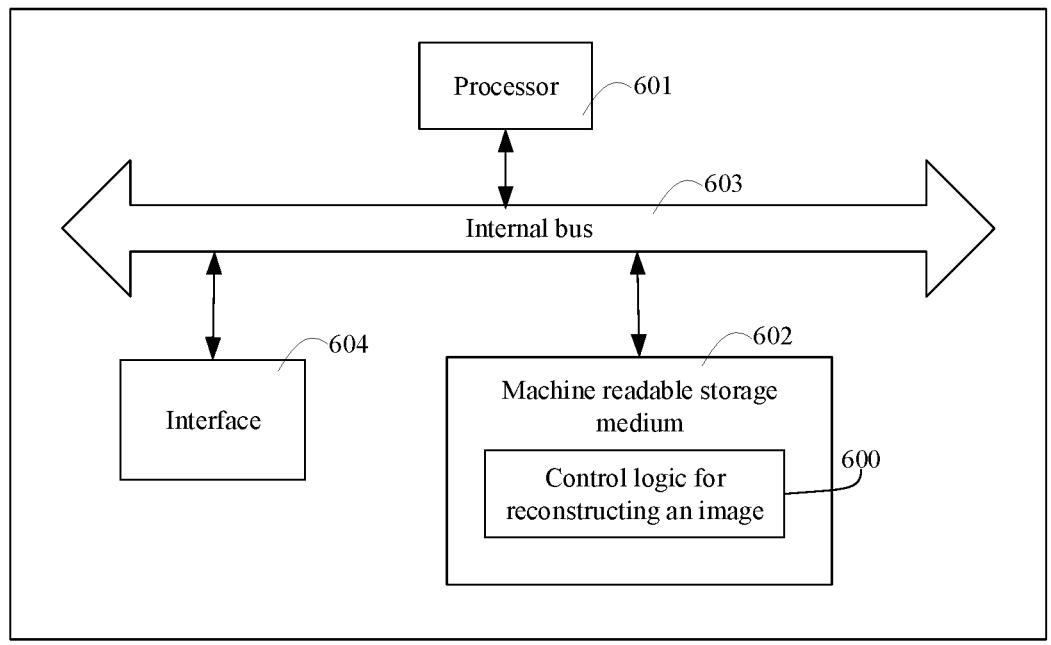
FIG. 6 is a schematic diagram illustrating a hardware structure of a device for reconstructing an image, according to an example of the present disclosure.

Referring to FIG. 6, the device for reconstructing an image may include a processor 601 and a machine-readable storage medium 602. The processor 601 is connected with the machine-readable storage medium 602 with an internal bus 603. In other possible implementations, the device may further include an external interface 604 so that the device can communicate with other devices or components.

In different examples, the machine-readable storage medium 602 may be a Random Access Memory (RAM), a volatile memory, a nonvolatile memory, a flash memory, a storage drive (e.g., hard disk drive), a solid state disk, any type of storage disk (e.g., optical disk, Digital Video Disk (DVD)), or a similar storage medium, or a combination thereof.

Figure 7:
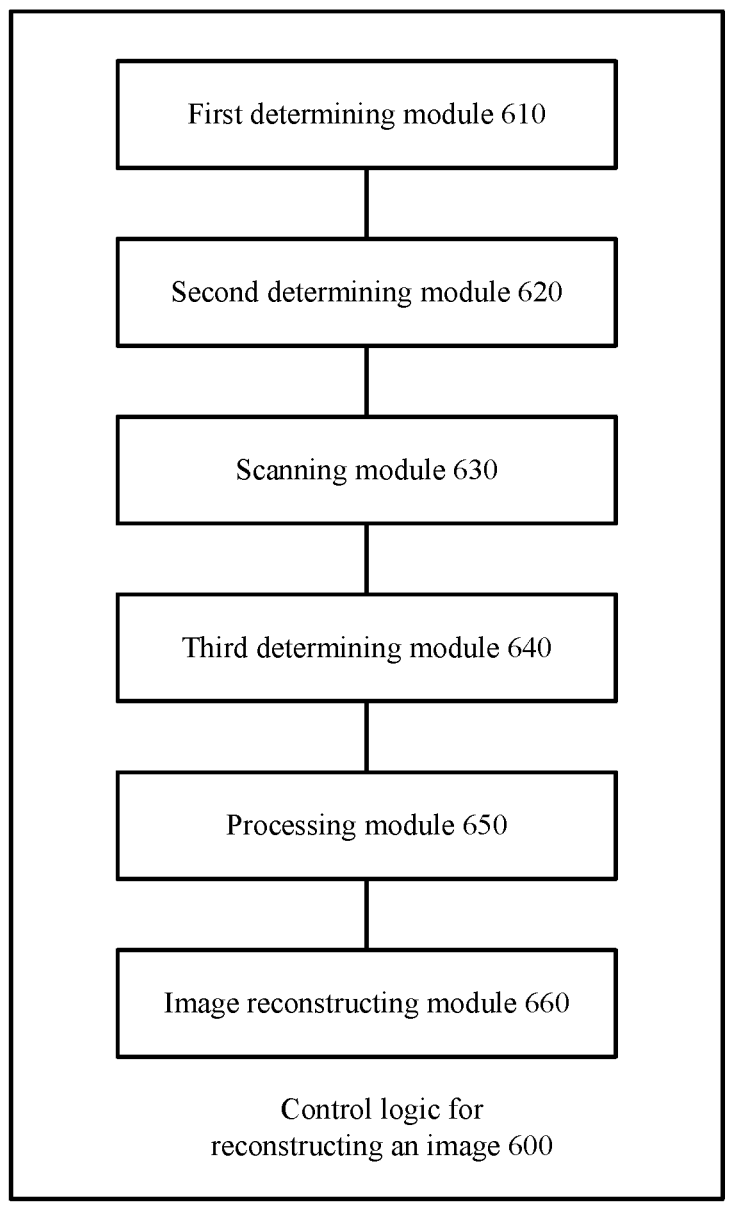
FIG. 7 is a schematic diagram illustrating a functional module of a control logic for reconstructing an image, according to an example of the present disclosure.

Further, machine-executable instructions corresponding to a control logic 600 for reconstructing an image are stored on the machine-readable storage medium 602. Functionally, the control logic 600 may include the following modules as shown in FIG. 7.

A first determining module 610 is configured to determine an initial angle and a final angle of an X-ray tube when a helical-half-scan is to be performed, where the helical-half-scan refers to a helical scan in which the X-ray tube emits X-rays only between the initial angle and the final angle during one circle of rotation of a gantry.

A second determining module 620 is configured to determine a pitch value of the helical-half-scan A scanning module 630 is configured to obtain scanning data of each of reconstructing points in a reconstructing position by performing the helical-half-scan on a detected region of a subject based on the initial angle and the final angle of the X-ray tube determined by the first determining module 610 and the pitch value determined by the second determining module 620.

A third determining module 640 is configured to determine a half-scan-weight and a helical weight of each of the reconstructing points in the reconstructing position.

A processing module 650 is configured to obtain weighted data by performing weighting on the scanning data of the reconstructing point with the half-scan-weight and the helical weight of the reconstructing point.

An image reconstructing module 660 is configured to reconstruct a CT image of the reconstructing position by performing back-projection on the weighted data.

In an example, the device for reconstructing an image further includes a helical-half-scan determining module, which is configured to determine that the helical-half-scan is to be performed when the detected region of the subject contains a skip region without X-ray radiation or a dual-energy scan is determined to be performed on the detected region of the subject.

In an example, the first determining module 610 is further configured to determine a position of the skip region and determine the initial angle and the final angle of the X-ray tube based on the position of the skip region, where an absolute value of a difference between the initial angle and the final angle of the X-ray tube is equal to or greater than a preset angle threshold. When the absolute value of the difference between the initial angle and the final angle of the X-ray tube is equal to the preset angle threshold, the obtained scanning data during one circle of rotation of the gantry is sufficient for reconstructing the CT image of the reconstructing position.

In another example, the first determining module 610 is further configured to select a kilovolt switching time length of the dual-energy scan, determine a ray-emitting angle interval length of the X-ray tube based on the kilovolt switching time length, and when any two angles of which an absolute value of a difference is smaller than the ray-emitting angle interval length and equal to or greater than a preset angle threshold, respectively determine the two angles as the initial angle and the final angle of the X-ray tube. Where when an absolute value of a difference between the initial angle and the final angle of the X-ray tube is equal to the preset angle threshold, the obtained scanning data during one circle of rotation of the gantry is sufficient for reconstructing the CT image of the reconstructing position.

In an example, the second determining module 620 is further configured to determine a maximum pitch value based on a reconstructing field of view of a CT device, a radius of rotation of the X-ray tube, a number of slices of a detector of the CT device and a single-slice thickness of the detector, and determine a value less than the maximum pitch value as the pitch value. When the helical-half-scan is performed according to the maximum pitch value, the obtained scanning data during one circle of rotation of the gantry is sufficient for reconstructing the CT image of the reconstructing position.

In an example, the third determining module 640 is further configured to determine whether the scanning data of the reconstructing point satisfies a preset image reconstructing condition, and determine the half-scan-weight and the helical weight of the reconstructing point when the scanning data of the reconstructing point satisfies the preset image reconstructing condition.

In an example, the third determining module 640 is further configured to determine the scanning data of the reconstructing point corresponding to a same energy level as second scanning data, determine a sampling angle of the second scanning data at each of sampling views, generate a slice position of the sampling angle relative to the reconstructing point based on a coordinate of the reconstructing point, a radius of rotation of the X-ray tube, a number of slices of a detector of a CT device and a single-slice thickness of the detector, and determine whether the second scanning data satisfies the preset image reconstructing condition based on the slice position of the sampling angle relative to the reconstructing point.

In an example, the third determining module 640 is further configured to determine a number of valid sampling angles of the reconstructing point based on the slice position of each of the sampling angles relative to the reconstructing point, and determine that the second scanning data satisfies the preset image reconstructing condition when the number of the valid sampling angles is greater than or equal to a preset number threshold.

In an example, the third determining module 640 is further configured to determine a number of sampling angles each of which the slice position is greater than or equal to 0 and less than or equal to the number of slices of the detector minus 1; and define the number of the sampling angles each of which the slice position is greater than or equal to 0 and less than or equal to the number of slices of the detector minus 1 as the number of valid sampling angles of the reconstructing point.

Details of the implementation process of the functions and effects of various modules in the above logical for reconstructing an image may be seen from the implementation process of corresponding steps in the above-described method, which will not be redundantly described herein.

The following description is further made on how the device for reconstructing an image executes the control logic 600 by taking software implementation for example. In this example, the control logic in the present disclosure may be construed as machine-executable instructions stored on the machine-readable storage medium 602. When the processor 601 in the device for reconstructing an image in the present disclosure executes the control logic, the processor 601 executes the above method of reconstructing an image by invoking the machine-executable instructions stored on the machine-readable storage medium 602.

Since the device examples substantially correspond to the method examples, a reference may be made to part of the descriptions of the method examples for the related part. The device examples described above are merely illustrative, where the units described as separate members may be or not be physically separated, and the members displayed as units may be or not be physical units, i.e., may be located in one place, or may be distributed to a plurality of network units. Part or all of the modules may be selected according to actual requirements to implement the objectives of the solutions in the embodiments. Those of ordinary skill in the art may understand and carry out them without creative work.

The present disclosure further provides a non-temporary machine-readable storage medium that stores machine-executable instructions executed by one or more processors. The machine-executable instructions can be executed by one or more processors as described above to implement the method of reconstructing an image as discussed above.

The foregoing is merely descriptions of part of examples of the present disclosure and not intended to limit the present disclosure. Any modifications, equivalent substitutions, adaptations made within the spirit and principles of the present disclosure shall be encompassed in the scope of protection the present disclosure.

What is claimed is:
1. A method of reconstructing an image, comprising:
when a helical-half-scan is to be performed, determining an initial angle and a final angle of an X-ray tube and a pitch value, wherein the helical-half-scan refers to a helical scan in which the X-ray tube emits X-rays between the initial angle and the final angle during one circle of rotation of a gantry;

obtaining scanning data of each of reconstructing points in a reconstructing position by performing the helical-half-scan on a detected region of a subject based on the determined initial angle, the final angle and the pitch value;

determining a respective half-scan-weight and a respective helical weight of each of the reconstructing points in the reconstructing position;

obtaining weighted data by performing weighting on the scanning data of each of the reconstructing points with the respective half-scan-weight and the respective helical weight of the reconstructing point; and reconstructing a Computed Tomography (CT) image of the reconstructing position by performing back-projection on the weighted data.

2. The method of claim 1, further comprising:
determining that the helical-half-scan is to be performed by determining that the detected region of the subject contains a skip region without X-ray radiation.

3. The method of claim 2, wherein determining the initial angle and the final angle of the X-ray tube comprises:
determining a position of the skip region; and
determining the initial angle and the final angle of the X-ray tube based on the position of the skip region, wherein an absolute value of a difference between the initial angle and the final angle of the X-ray tube is equal to or greater than a preset angle threshold, and
wherein the obtained scanning data during one circle of rotation of the gantry is sufficient for reconstructing the CT image of the reconstructing position.

4. The method of claim 1, further comprising:
determining that the helical-half-scan is to be performed by determining that a dual-energy scan is to be performed on the detected region of the subject.

5. The method of claim 4, wherein determining the initial angle and the final angle of the X-ray tube comprises:
selecting a kilovolt switching time length of the dual-energy scan;
determining a ray-emitting angle interval length of the X-ray tube based on the kilovolt switching time length; and
determining two angles as the initial angle and the final angle of the X-ray tube, respectively, wherein an absolute value of a difference of the two angles is smaller than the ray-emitting angle interval length and equal to or greater than a preset angle threshold, and
wherein the obtained scanning data during one circle of rotation of the gantry is sufficient for reconstructing the CT image of the reconstructing position.

6. The method of claim 1, wherein determining the pitch value comprises:
determining a maximum pitch value based on a reconstructing field of view of a CT device, a radius of rotation of the X-ray tube, a number of slices of a detector of the CT device and a single-slice thickness of the detector; and
determining a value less than the maximum pitch value as the pitch value,
wherein, when the helical-half-scan is performed according to the maximum pitch value, the obtained scanning data during one circle of rotation of the gantry is sufficient for reconstructing the CT image of the reconstructing position.

7. The method of claim 1, wherein determining the half-scan-weight and the helical weight of the reconstructing point comprises:
determining whether the scanning data of the reconstructing point satisfies a preset image reconstructing condition; and
in response to determining that the scanning data of the reconstructing point satisfies the preset image reconstructing condition, determining the half-scan-weight and the helical weight of the reconstructing point.

8. The method of claim 7, wherein determining whether the scanning data of the reconstructing point satisfies the preset image reconstructing condition comprises:
determining the scanning data of the reconstructing point corresponding to a same energy level as second scanning data;
determining a sampling angle of the second scanning data at each of sampling views;
generating a slice position of the sampling angle relative to the reconstructing point based on a coordinate of the reconstructing point, a radius of rotation of the X-ray tube, a number of slices of a detector of a CT device and a single-slice thickness of the detector; and
determining whether the second scanning data satisfies the preset image reconstructing condition based on the slice position of the sampling angle relative to the reconstructing point.

9. The method of claim 8, wherein determining whether the second scanning data satisfies the preset image reconstructing condition based on the slice position of the sampling angle relative to the reconstructing point comprises:
determining a number of valid sampling angles of the reconstructing point based on the slice position of each of the sampling angles relative to the reconstructing point; and
determining whether the second scanning data satisfies the preset image reconstructing condition by determining whether the number of the valid sampling angles is greater than or equal to a preset number threshold.

10. The method of claim 9, further comprising:
determining a number of sampling angles each of which the slice position is no less than 0 and no greater than the number of slices of the detector minus 1, and in response,
defining the number of the sampling angles as the number of valid sampling angles of the reconstructing point.

11. A device for reconstructing an image, comprising:
at least one processor; and
at least one non-transitory machine-readable storage medium coupled to the at least one processor having machine-executable instructions stored thereon that, when executed by the at least one processor, cause the at least one processor to perform operations comprising:
when a helical-half-scan is to be performed, determining an initial angle and a final angle of an X-ray tube and a pitch value, wherein the helical-half-scan refers to a helical scan in which the X-ray tube emits X-rays between the initial angle and the final angle during one circle of rotation of a gantry;
obtaining scanning data of each of reconstructing points in a reconstructing position by performing the helical-half-scan on a detected region of a subject based on the determined initial angle, the final angle and the pitch value;

determining a half-scan-weight and a helical weight of each of the reconstructing points in the reconstructing position;

obtaining weighted data by performing weighting on the scanning data of each of the reconstructing points with the half-scan-weight and the helical weight of the reconstructing point; and reconstructing a Computed Tomography (CT) image of the reconstructing position by performing back-projection on the weighted data.

12. The device of claim 11, wherein the operations further comprise:

determining that the helical-half-scan is to be performed by determining that the detected region of the subject contains a skip region without X-ray radiation.

13. The device of claim 12, wherein determining the initial angle and the final angle of the X-ray tube comprises:

determining a position of the skip region; and determining the initial angle and the final angle of the X-ray tube based on the position of the skip region, wherein an absolute value of a difference between the initial angle and the final angle of the X-ray tube is equal to or greater than a preset angle threshold, and wherein the obtained scanning data during one circle of rotation of the gantry is sufficient for reconstructing the CT image of the reconstructing position.

14. The device of claim 11, wherein the operations further comprise:

determining that the helical-half-scan is to be performed by determining that a dual-energy scan is to be performed on the detected region of the subject.

15. The device of claim 14, wherein determining the initial angle and the final angle of the X-ray tube comprises:

selecting a kilovolt switching time length of the dual-energy scan;

determining a ray-emitting angle interval length of the X-ray tube based on the kilovolt switching time length; and determining two angles as the initial angle and the final angle of the X-ray tube, respectively, wherein an absolute value of a difference of the two angles is smaller than the ray-emitting angle interval length and equal to or greater than a preset angle threshold, and wherein the obtained scanning data during one circle of rotation of the gantry is sufficient for reconstructing the CT image of the reconstructing position.

16. The device of claim 11, wherein determining the pitch value comprises:

determining a maximum pitch value based on a reconstructing field of view of a CT device, a radius of rotation of the X-ray tube, a number of slices of a detector of the CT device and a single-slice thickness of the detector; and determining a value less than the maximum pitch value as the pitch value;

wherein, when the helical-half-scan is performed according to the maximum pitch value, the obtained scanning data during one circle of rotation of the gantry is sufficient for reconstructing the CT image of the reconstructing position.

17. The device of claim 11, wherein determining the half-scan-weight and the helical weight of the reconstructing point comprises:

determining whether the scanning data of the reconstructing point satisfies a preset image reconstructing condition; and in response to determining that the scanning data of the reconstructing point satisfies the preset image reconstructing condition, determining the half-scan-weight and the helical weight of the reconstructing point.

18. The device of claim 17, wherein determining whether the scanning data of the reconstructing point satisfies the preset image reconstructing condition comprises:

determining the scanning data of the reconstructing point corresponding to a same energy level as second scanning data;

determining a sampling angle of the second scanning data at each of sampling views;

generating a slice position of the sampling angle relative to the reconstructing point based on a coordinate of the reconstructing point, a radius of rotation of the X-ray tube, a number of slices of a detector of a CT device and a single-slice thickness of the detector; and determining whether the second scanning data satisfies the preset image reconstructing condition based on the slice position of the sampling angle relative to the reconstructing point.

19. The device of claim 18, wherein determining whether the second scanning data satisfies the preset image reconstructing condition based on the slice position of the sampling angle relative to the reconstructing point comprises:

determining a number of valid sampling angles of the reconstructing point based on the slice position of each of the sampling angles relative to the reconstructing point; and determine whether the second scanning data satisfies the preset image reconstructing condition by determining whether the number of the valid sampling angles is greater than or equal to a preset number threshold.

20. The device of claim 19, wherein the operations further comprise:

determining a number of sampling angles each of which the slice position is no less than 0 and no greater than the number of slices of the detector minus 1, and in response, defining the number of the sampling angles as the number of valid sampling angles of the reconstructing point.

* * * * *